United States Patent
Yamada et al.

(10) Patent No.: US 9,808,032 B2
(45) Date of Patent: Nov. 7, 2017

(54) NON-BURNING TYPE FLAVOR INHALER WITH A POWER CONTROLLER AS A FUNCTION OF PUFF ACTIONS

(71) Applicant: JAPAN TOBACCO INC., Tokyo (JP)

(72) Inventors: Manabu Yamada, Tokyo (JP);
Manabu Takeuchi, Tokyo (JP);
Takeshi Shinkawa, Tokyo (JP);
Hirofumi Matsumoto, Tokyo (JP);
Takuma Nakano, Tokyo (JP)

(73) Assignee: JAPAN TOBACCO INC., Tokyo (JP)

( * ) Notice: Subject to any disclaimer, the term of this patent is extended or adjusted under 35 U.S.C. 154(b) by 65 days.

(21) Appl. No.: 15/084,305

(22) Filed: Mar. 29, 2016

(65) Prior Publication Data
US 2016/0206005 A1 Jul. 21, 2016

Related U.S. Application Data

(63) Continuation of application No. PCT/JP2014/075610, filed on Sep. 26, 2014.

(30) Foreign Application Priority Data

Sep. 30, 2013 (JP) .................................. 2013-204190
Jan. 29, 2014 (JP) .................................. 2014-014190
(Continued)

(51) Int. Cl.
*A24F 13/00* (2006.01)
*A24F 47/00* (2006.01)
(Continued)

(52) U.S. Cl.
CPC ............ *A24F 47/008* (2013.01); *A24F 47/00* (2013.01); *A61M 11/042* (2014.02);
(Continued)

(58) Field of Classification Search
CPC .......... A24F 47/00; A24F 47/008; A24F 1/00; A24F 1/02; A24F 1/24; A24F 15/00; A24F 19/10; A24F 13/22; A24F 19/005
(Continued)

(56) References Cited

U.S. PATENT DOCUMENTS

2008/0092912 A1    4/2008 Robinson et al.
2013/0340750 A1*  12/2013 Thorens ................ A24F 47/008
                                                               128/202.21
(Continued)

FOREIGN PATENT DOCUMENTS

EP        0430559 A2    6/1991
EP        0 845 220 A1  6/1998
(Continued)

OTHER PUBLICATIONS

International Search Report for PCT/JP2014/075610 dated Dec. 16, 2014.
(Continued)

*Primary Examiner* — Chandrika Prasad
(74) *Attorney, Agent, or Firm* — Birch, Stewart, Kolasch & Birch, LLP

(57) ABSTRACT

A non-burning type flavor inhaler includes: an aerosol source that generates an aerosol; an atomizer that atomizes the aerosol source without burning; a power source that supplies power to the atomizer; and a control unit that controls a power amount supplied from the power source to the atomizer. The control unit increases the power amount supplied to the atomizer stepwise from a reference power amount along with an increase in the number of puff actions for inhaling the aerosol.

14 Claims, 12 Drawing Sheets

(30) Foreign Application Priority Data

Jan. 29, 2014 (JP) .................................. 2014-014201
Jan. 29, 2014 (JP) .................................. 2014-014208

(51) Int. Cl.
| | |
|---|---|
| *H05B 1/02* | (2006.01) |
| *H05B 3/00* | (2006.01) |
| *A61M 15/06* | (2006.01) |
| *A61M 11/04* | (2006.01) |
| *A61M 16/00* | (2006.01) |

(52) U.S. Cl.
CPC ........... *A61M 15/06* (2013.01); *H05B 1/0202* (2013.01); *H05B 3/0014* (2013.01); *A61M 2016/0021* (2013.01); *A61M 2016/0027* (2013.01); *A61M 2205/3653* (2013.01); *A61M 2205/584* (2013.01); *A61M 2205/8206* (2013.01)

(58) Field of Classification Search
USPC ........ 131/329, 330, 185, 193, 194, 234, 260
See application file for complete search history.

(56) References Cited

U.S. PATENT DOCUMENTS

| | | | | |
|---|---|---|---|---|
| 2014/0182608 | A1* | 7/2014 | Egoyants | A24F 47/008 131/328 |
| 2014/0270727 | A1* | 9/2014 | Ampolini | A24F 47/008 392/387 |
| 2015/0313284 | A1* | 11/2015 | Liu | H05B 1/0244 131/329 |
| 2016/0213066 | A1* | 7/2016 | Zitzke | A24F 47/008 |

FOREIGN PATENT DOCUMENTS

| | | |
|---|---|---|
| EP | 2460423 A1 | 6/2012 |
| JP | 2010-506594 A | 3/2010 |
| WO | WO 9418860 A1 | 9/1994 |
| WO | WO 97/48293 A1 | 12/1997 |
| WO | WO 2012/109371 A2 | 8/2012 |
| WO | WO 2013/060781 A1 | 5/2013 |
| WO | WO 2013/060784 A2 | 5/2013 |

OTHER PUBLICATIONS

European Patent Office, "Communication with Extended Search Report," issued in connection with European Patent Application No. 14847127.9, dated Mar. 3, 2017.

* cited by examiner

FIG. 4

| PUFF STATE | NON-PUFF STATE #1 | PUFF STATE #1 | NON-PUFF STATE #2 | PUFF STATE #2 | NON-PUFF STATE #3 | PUFF STATE #3 | NON-PUFF STATE #4 | PUFF STATE #4 |
|---|---|---|---|---|---|---|---|---|
| LIGHT-EMITTING MODE | LIGHT-EMITTING MODE #2-1 | LIGHT-EMITTING MODE #1 | LIGHT-EMITTING MODE #2-1 | LIGHT-EMITTING MODE #1 | LIGHT-EMITTING MODE #2-1 | LIGHT-EMITTING MODE #1 | LIGHT-EMITTING MODE #2-1 | LIGHT-EMITTING MODE #1 |

| PUFF STATE | NON-PUFF STATE #5 | PUFF STATE #5 | NON-PUFF STATE #6 | PUFF STATE #6 | NON-PUFF STATE #7 | PUFF STATE #7 | NON-PUFF STATE #8 | PUFF STATE #8 | NON-PUFF STATE #9 OR MORE | PUFF STATE #9 OR MORE |
|---|---|---|---|---|---|---|---|---|---|---|
| LIGHT-EMITTING MODE | LIGHT-EMITTING MODE #2-2 | LIGHT-EMITTING MODE #1 | LIGHT-EMITTING MODE #2-2 | LIGHT-EMITTING MODE #1 | LIGHT-EMITTING MODE #2-2 | LIGHT-EMITTING MODE #1 | LIGHT-EMITTING MODE #2-3 | LIGHT-EMITTING MODE #1 | EMISSION END MODE | LIGHT-EMITTING MODE #1 |

FIG. 5

| PUFF STATE | PUFF STATE #1 | NON-PUFF STATE #1 | PUFF STATE #2 | NON-PUFF STATE #2 | PUFF STATE #3 | NON-PUFF STATE #3 | PUFF STATE #4 | NON-PUFF STATE #4 | PUFF STATE #4 |
|---|---|---|---|---|---|---|---|---|---|
| LIGHT-EMITTING MODE | LIGHT-EMITTING MODE #2-1 | LIGHT-EMITTING MODE #1-1 | LIGHT-EMITTING MODE #2-1 | LIGHT-EMITTING MODE #1-1 | LIGHT-EMITTING MODE #2-1 | LIGHT-EMITTING MODE #1-1 | LIGHT-EMITTING MODE #2-1 | LIGHT-EMITTING MODE #1-1 |

| PUFF STATE | PUFF STATE #5 | NON-PUFF STATE #5 | PUFF STATE #6 | NON-PUFF STATE #6 | PUFF STATE #7 | NON-PUFF STATE #7 | PUFF STATE #8 | NON-PUFF STATE #8 | NON-PUFF STATE #9 OR MORE | PUFF STATE #9 OR MORE |
|---|---|---|---|---|---|---|---|---|---|---|
| LIGHT-EMITTING MODE | LIGHT-EMITTING MODE #2-2 | LIGHT-EMITTING MODE #1-2 | LIGHT-EMITTING MODE #2-2 | LIGHT-EMITTING MODE #1-2 | LIGHT-EMITTING MODE #2-2 | LIGHT-EMITTING MODE #1-2 | LIGHT-EMITTING MODE #2-3 | LIGHT-EMITTING MODE #1-3 | EMISSION END MODE | LIGHT-EMITTING MODE #1-4 |

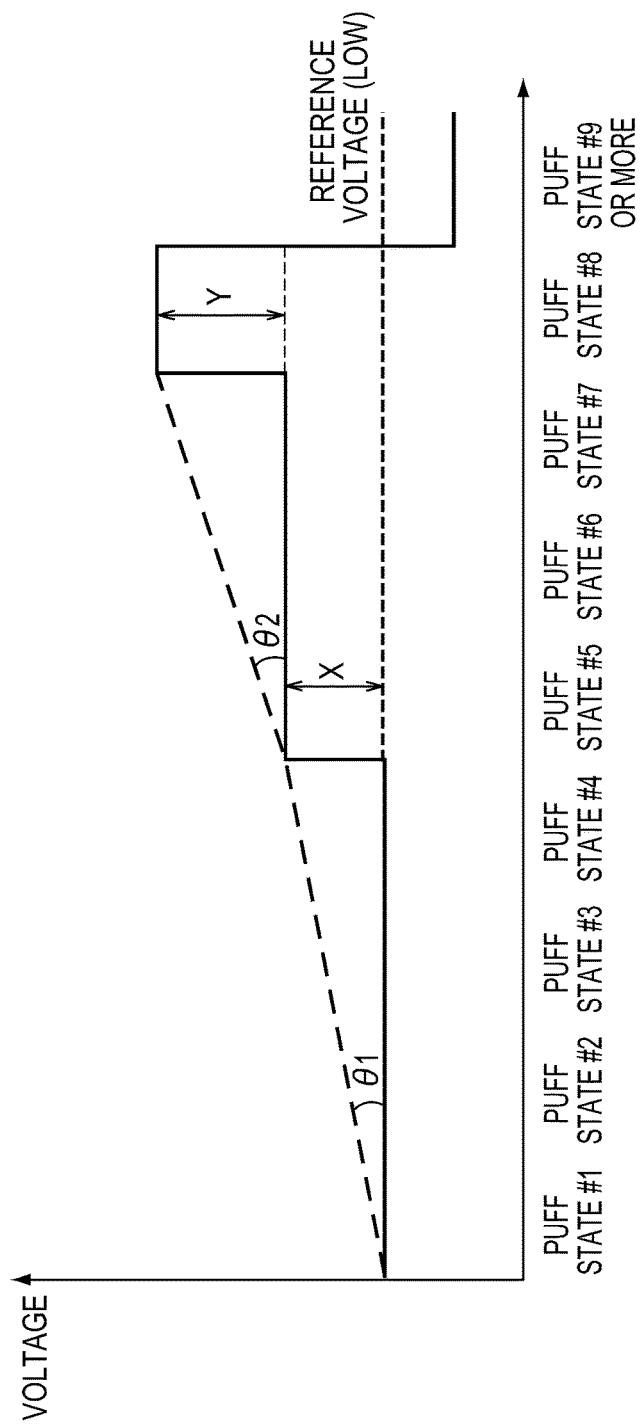

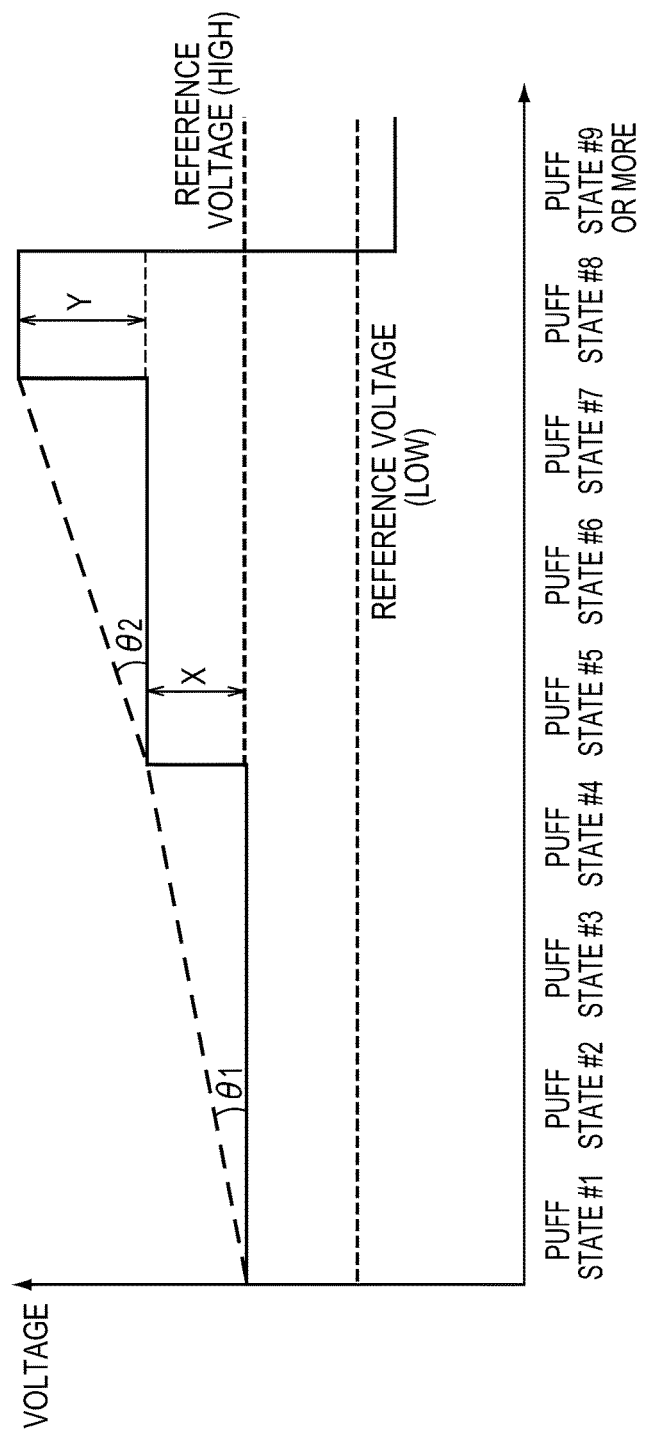

NON-BURNING TYPE FLAVOR INHALER WITH A POWER CONTROLLER AS A FUNCTION OF PUFF ACTIONS

CROSS REFERENCE TO RELATED APPLICATIONS

This application is a Continuation of PCT International Application No. PCT/JP2014/075610, filed on Sep. 26, 2014, which claims priority under 35 U.S.C. §119(a) to Japanese Patent Application No. 2013-204190, filed in Japan on Sep. 30, 2013, Japanese Patent Application No. 2014-014190, filed in Japan on Jan. 29, 2014, Japanese Patent Application No. 2014-014201, filed in Japan on Jan. 29, 2014, Japanese Patent Application No. 2014-014208, filed in Japan on Jan. 29, 2014, all of which are hereby expressly incorporated by reference into the present application.

TECHNICAL FIELD

The present invention relates to a non-burning type flavor inhaler having a shape extending from a non-inhalation end toward an inhalation end along a predetermined direction.

BACKGROUND ART

A non-burning type flavor inhaler for inhaling flavor without burning has been known. The non-burning type flavor inhaler has a shape extending from a non-inhalation end toward an inhalation end along a predetermined direction. The non-burning type flavor inhaler comprises an aerosol source for generating an aerosol, a heat source for heating an aerosol source without burning, and a power source for supplying power to a heat source (for example, Patent Literature 1).

As a puff action of inhaling an aerosol is different for each user, it has been studied to make the supplied amount of aerosol (TPM: Total Particulate Matter) per one puff action constant. For example, a technique to keep a temperature of a heat source constant by controlling power supplied to a heat source (voltage applied to a heat source) per one puff action has been proposed (for example, Patent Literatures 2 and 3). Such a technique suppresses a variation in the supplied amount of aerosol between puff actions.

CITATION LIST

Patent Literature

Patent Literature 1: Japanese PCT National Publication No. 2010-506594
Patent Literature 2: International Publication No. 2013/060781
Patent Literature 3: International Publication No. 2013/060784

SUMMARY OF THE INVENTION

A first feature is summarized as a non-burning type flavor inhaler having a shape extending from a non-inhalation end toward an inhalation end along a predetermined direction, comprising: an aerosol source that generates an aerosol; an atomizer that atomizes the aerosol source without burning; a power source that supplies power to the atomizer; and a control unit that controls a power amount supplied from the power source to the atomizer, wherein the control unit increases the power amount supplied to the atomizer stepwise from a reference power amount along with an increase in the number of puff actions for inhaling the aerosol.

A second feature according to the first feature is summarized as that the control unit controls a first mode using a first reference power amount as the reference power amount, and a second mode using a second reference power amount greater than the first reference power amount.

A third feature according to any one of the first and second features is summarized as that the control unit controls the power source to supply the atomizer with the power amount smaller than the reference power amount, when the puff action is performed after the number of puff actions exceeds a predetermined number.

A fourth feature according to the third feature is summarized as that the control unit turns off the power of the non-burning type flavor inhaler, when a predetermined time elapse after the number of puff actions exceeds the predetermined number.

A fifth feature according to any one of the first to fourth features is summarized as that the control unit increases a gradient of the power amount supplied to the atomizer along with the increase in the number of puff actions of inhaling the aerosol.

A sixth feature according to any one of the first to fifth features is summarized as the non-burning type flavor inhaler comprising a light-emitting element, wherein the control unit controls the light-emitting element in a first light-emitting mode in a puff state inhaling the aerosol, and controls the light-emitting element in a second light-emitting mode different from the first light-emitting mode in a non-puff state not inhaling the aerosol, and the second light-emitting mode changes according to the number of puff actions for inhaling the aerosol, and a timing of increasing the power amount supplied to the atomizer is synchronized with a timing of changing the second light-emitting mode.

A seventh feature according to any one of the first to sixth features is summarized as that the number of puff actions is corrected by a value defined by the time required per one puff action and the power amount supplied to the heat source.

An eighth feature according to the second feature is summarized as that a switching between the first mode and the second mode is performed by an operation of a push-button or a touch sensor.

A ninth feature according to the eighth feature is summarized as that the power of the non-burning type flavor inhaler is turned on by the operation of the switching between the first mode and the second mode.

A tenth feature according to any one of the first to ninth features is summarized as the non-burning type flavor inhaler comprising a tobacco source provided at the non-inhalation end side than the aerosol source.

An eleventh feature according to the tenth feature is summarized as that the tobacco source includes a stabilization agent stabilizes the delivery of nicotine component included in the tobacco source, and the stabilization agent has characteristics that a solubility parameter distance to the nicotine component is 17 or less and a vapor pressure at 25° C. is 1 mmHg or less.

A twelfth feature according to any one of the first to eleventh features is summarized as the non-burning type flavor inhaler comprising a hardware switch for performing at least one of turning on and turning off the non-burning type flavor inhaler.

A thirteenth feature according to any one of the first to twelfth features is summarized as that the number of puff actions reset in response to any one of turning on and turning off the non-burning type flavor inhaler.

A fourteenth feature according to any one of the first to twelfth features is summarized as that the atomizer is a heat source that heats the aerosol source without burning.

BRIEF DESCRIPTION OF THE DRAWINGS

FIG. 4 is a diagram showing an example of a light-emitting mode according to a first embodiment.

FIG. 5 is a diagram showing an example of a light-emitting mode according to a first embodiment.

FIG. 6 is a diagram showing an example of power control in a puff action series according to a first embodiment.

FIG. 7 is a diagram showing an example of power control in a puff action series according to a first embodiment.

DESCRIPTION OF EMBODIMENTS

Figure 1:
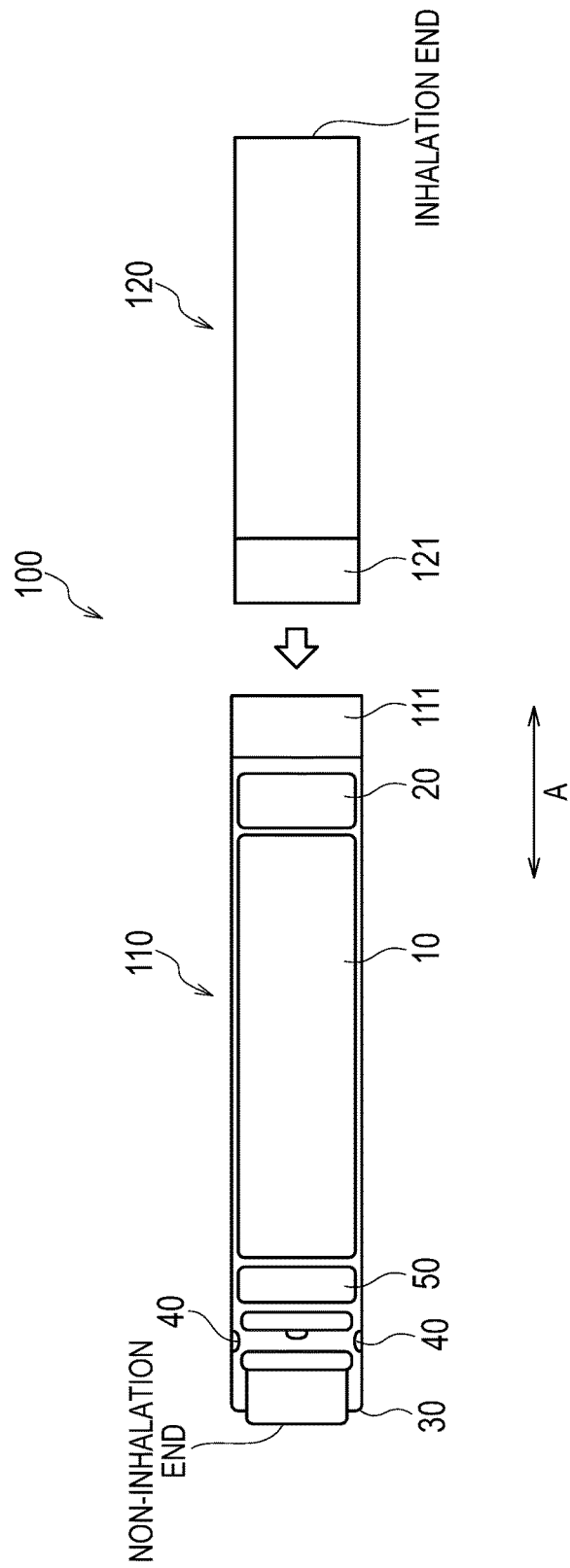
FIG. 1 is a diagram showing a non-burning type flavor inhaler 100 according to a first embodiment.

Hereinafter, embodiments of the present invention will be described. In the following description of the drawings, the same or similar parts are denoted by the same or similar reference numerals. It is noted that the drawings are schematic, and the ratios of dimensions and the like are different from the actual ones.

Therefore, specific dimensions and the like should be determined by referring to the following description. Of course, the drawings include the parts with different dimensions and ratios.

[Overview of Embodiment]

The inventors have studied intensively and noted that an initial puff action and an end puff action are different in a general cigarette that generates an aerosol along with burning. In an initial puff action, a burning position is apart from an inhalation end, and an aerosol is easily filtered in a cigarette. Therefore, the amount of aerosol reaching a user is decreased. On the other hand, in an end puff action, a burning position is close to an inhalation end, and an aerosol is hardly filtered in a cigarette. Therefore, the amount of aerosol reaching a user is increased.

From such a point of view, the inventors have acquired new knowledge that it is impossible to realize a feeling of use like a general cigarette even when the amount of aerosol inhaled per one puff action is constant.

A non-burning type flavor inhaler according to an embodiment has a shape extending from a non-inhalation end toward an inhalation end along a predetermined direction. The non-burning type flavor inhaler comprises an aerosol source that generates an aerosol, an atomizer that atomizes the aerosol source without burning, a power source that supplies power to the heat source, and a control unit that controls a power amount supplied from the power source to the atomizer. The control unit increases the power amount supplied to the atomizer stepwise from a reference power amount along with an increase in the number of puff actions for inhaling the aerosol.

In the embodiment, the control unit increases the power amount supplied to a heat source stepwise from a reference power amount along with an increase in the number of puff actions of inhaling aerosol. Thus, it is possible to bring the supplied amount of aerosol close to that of a general cigarette, and realize a feeling of use like a feeling of use of a general cigarette.

[First Embodiment]

(Non-Burning Type Flavor Inhaler)

Figure 2:
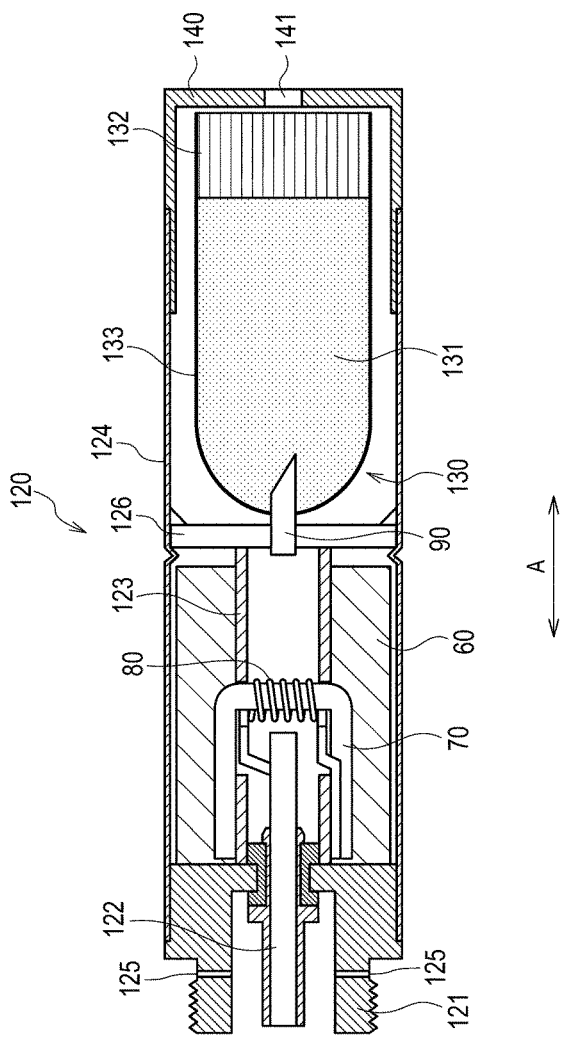
FIG. 2 is a diagram showing an atomizing unit 120 according to a first embodiment.

Hereinafter, a non-burning type flavor inhaler according to a first embodiment will be explained. FIG. 1 is a diagram showing a non-burning type flavor inhaler 100 according to a first embodiment. FIG. 2 is a diagram showing an atomizing unit 120 according to a first embodiment.

In the first embodiment, the non-burning type flavor inhaler 100 is a device for inhaling flavor without burning, and has a shape extending along a predetermined direction A that is a direction from a non-inhalation end toward an inhalation end.

As showed in FIG. 1, the non-burning type flavor inhaler 100 comprises an electrical unit 110 and an atomizing unit 120. The electrical unit 110 has a female connector 111 in a part adjacent to the atomizing unit 120. The atomizing unit 120 has a male connector 121 in a part adjacent to the electrical unit 110. The female connector 111 has a spiral groove extending along a direction orthogonal to the predetermined direction A. The male connector 121 has a spiral projection extending along a direction orthogonal to the predetermined direction A. By screwing the male connector 121 into the female connector 111, the atomizing unit 120 and the electrical unit 110 are connected each other. The atomizing unit 120 is configured to be attachable/detachable to/from the electrical unit 110.

The electrical unit 110 comprises a power source 10, a sensor 20, a pushbutton 30, a light-emitting element 40 and a control circuit 50.

The power source 10 is a lithium-ion battery, for example. The power source 10 supplies power required for operating the non-burning type flavor inhaler 100. For example, the power source 10 supplies power to the sensor 20, the light-emitting element 40 and the control circuit 50. Further, the power source 10 applies power to a heat source 80 described later.

The sensor 20 detects a wind pressure generated by a user's inhaling action. Specifically, the sensor 20 detects a negative pressure when the air is inhaled toward the atomizing unit 120. The sensor 20 is not particularly limited, but may be composed of a piezoelectric element.

The pushbutton 30 is configured to be pressed into the inhalation end side along the predetermined direction A. For example, by a predetermined action of the pushbutton 30 (i.e. an action for continuously pressing the pushbutton 30 over a predetermined number of times), the power of the non-burning type flavor inhaler 100 is turned on. When the power of the non-burning type flavor inhaler 100 is turned on, the power is supplied to the control circuit 50 from the power source 10 and the power is supplied to the sensor 20 and light-emitting element 40 from the power source 10 via the control circuit 50. Note that the power supply to the heater 80 is performed when the power is turned on and also the user's inhaling action is detected by the sensor 20. That is, the power supply to the heater 80 is not performed in a non-inhalation state that the aerosol is not inhaled.

Moreover, by a predetermined action of the pushbutton 30 (i.e. an action for long press of the pushbutton 30), the power of the non-burning type flavor inhaler 100 may be turned off. Since the power of the non-burning type flavor inhaler 100 is turned off by the predetermined action of the pushbutton 30, consumption power can be decreased when the non-burning type flavor inhaler 100 is not used.

The push button 30 may be a configuration for performing at least one of turning on or turning off the power of the non-burning type flavor inhaler 100.

The light-emitting element 40 is a light source such as an LED and an electric lamp. The light-emitting element 40 is provided on a sidewall extending along a predetermined direction. The light-emitting element 40 is preferably provided in the vicinity of the non-inhalation end. Thus, compared with a case where a light-emitting element is provided in the vicinity of the non-inhalation end on an axial line in the predetermined direction A, a user can easily recognize a light-emitting pattern of the light-emitting element 40 during an inhalation action. A light-emitting pattern of the light-emitting element 40 is a pattern to notify a user of a state of the non-burning type flavor inhaler 100.

The control circuit 50 controls the operation of the non-burning type flavor inhaler 100. In particular, the control circuit 50 controls a light-emitting pattern of the light-emitting element 40, and controls power amount supplied to a heat source 80.

The atomizing unit 120 comprises, as showed in FIG. 2, a holder 60, an absorber 70, a heat source 80 and a breaker 90. The atomizing unit 120 comprises a capsule unit 130 and an inhalation unit 140. The atomizing unit 120 has an air inlet hole 125 for taking outside air inside, an airflow path 122 that communicates with the electrical unit 110 (sensor 20) via the male connector 121, and a ceramic 123 that is arranged in a cylindrical shape. The atomizing unit 120 has a cylindrical outer wall 124 forming the outer shape of the atomizing unit 120. A space surrounded by the ceramic 123 forms an airflow path. The ceramic 123 contains alumina, for example, as a main component.

The holder 60 has a cylindrical shape, and holds the aerosol source for generating aerosol. The aerosol source is liquid such as propylene glycol and glycerin. The holder 60 is composed of a porous body impregnated with an aerosol source, for example. The porous body is a resin web, for example.

Further, in the first embodiment, the ceramic 123 is arranged inside the holder 60, suppressing volatilization of the aerosol source held by the holder 60.

The absorber 70 is provided adjacent to the holder 60, and is composed of a substance to absorb the aerosol source from the holder 60. The absorber 70 is made of glass fiber, for example.

The heat source 80 heats the aerosol source without burning. For example, the heat source 80 is a heating wire wound around the absorber 70. The heat source 80 heats the aerosol source absorbed by the absorber 70.

The breaker 90 is a member for breaking a part of predetermined film 133 in the state that the capsule unit 130 is mounted. In the embodiment, the breaker 90 is held by a partition member 126 for partitioning the atomizing unit 120 and the capsule unit 130. The partition member 126 is made of Polyacetal resin. The breaker 90 is a hallow cylindrical needle extending along a predetermined direction A, for example. By piercing a tip of the hollow needle into a predetermined film 133, a part of the predetermined film 133 is broken. Further, an inner space of the hollow needle forms an airflow path that communicates pneumatically the atomizing unit 120 with the capsule unit 130. It is preferable that a mesh having a roughness of not passing a material composing the flavor source 131 is provided inside the hollow needle. The roughness of the mesh is 80 meshes or more and 200 meshes or less, for example.

In such a case, the insertion depth of the hollow needle into the capsule unit 130 is preferably 1.0 mm or more and 5.0 mm or less, more preferably, 2.0 mm or more and 3.0 mm or less. At this insertion depth, the parts except a desired portion are not broken, suppressing detachment of the flavor source 131 filled in the space which is partitioned by the predetermined film 133 and the filter 132. Furthermore, since the detachment of the hollow needle from the space is suppressed, a proper airflow path to the filter 132 from the hollow needle can be preferably maintained.

In a vertical section with respect to the predetermined direction A, a sectional area of a vertical needle is preferably 2.0 mm$^2$ or more and 3.0 mm$^2$ or less. Thus, the flavor source 131 is prevented from falling off the capsule unit 130 when the hollow needle is removed.

The tip of the hollow needle preferable has an inclination of 30° or more and 45° or less with respect to the vertical direction to the predetermined direction A.

However, the embodiment is not limited to this. The breaker 90 may be a part adjacent to the predetermined film 133 in a state that the capsule unit 130 is mounted. A part of the predetermined film 133 may be broken by a pressure applied to such a part by a user.

The capsule unit 130 is configured to be attachable/detachable to/from the main body unit. The capsule unit 130 comprises a flavor source 131, a filter 132, and a predetermined film 133. The flavor source 131 is filled in a space partitioned by the predetermined film 133 and the filter 132. The main body unit is a unit that is composed of parts other except the capsule unit 130. For example, the main body unit includes the electrical unit 110, the holder 60, the absorber 70 and the heat source 80.

The flavor source 131 is provided on the inhalation end side than the holder 60 holding the aerosol source, and generates flavor inhaled by a user together with aerosol generated by the aerosol source. It is noted that the flavor source 131 is composed of a solid substance so as not to flow out of the space partitioned by the predetermined film 133 and the filter 132. As a flavor source 131, it is possible to use shredded tobacco, a molded body of granulated tobacco material, and a molded body formed into a sheet tobacco material. The flavor source 131 may be composed of a plant other than tobacco (for example, mint, herbs, and the like). The flavor source 131 may be given flavors such as menthol.

When the flavor source 131 is composed of tobacco material, as the tobacco material is apart from the heat source 80, it is possible to inhale the flavor without heating the tobacco material. In other words, it is noted that inhalation of unwanted substance generated by heating the tobacco material is suppressed.

In the first embodiment, the amount of the flavor source 131 filled in the space partitioned by the filter 132 and the predetermined film 133 is preferably 0.15 g/cc or more and 1.00 g/cc or less. The volume occupancy of the flavor source 131 in the space partitioned by the filter 132 and the predetermined film 133 is preferably 50% or more and 100% or less. The volume of the space partitioned by the filter 132 and the predetermined film 133 is preferably 0.6 ml or more and 1.5 ml or less. In such conditions, the flavor source 131 can be contained to the extent enough to enable a user to taste flavor while maintaining an appropriate size of the capsule unit 130.

In the state where a part of the predetermined film 133 is broken by the breaker 90 and where the atomizing unit 120 communicates with the capsule unit 130, when air is inhaled from a tip portion (non-broken portion) of the capsule unit 130 to a distal end of the filter 132 at a flow rate of 1050 cc/min, an airflow resistance (pressure loss) of the capsule unit 130 is preferably 10 mmAq or more and 100 mmAq or less, as a whole, more preferably, 20 mmAq or more and 90 mmAq or less. By setting the airflow resistance of the flavor source 131 to the above preferable range, aerosol is prevented from being overly filtered by the flavor source 131, and thus flavor can be efficiently supplied to a user. Incidentally, 1 mmAq corresponds to 9.80665 Pa, and the airflow resistance can be expressed by Pa.

The filter 132 is adjacent to the inhalation end side with respect to the flavor source 131, and is composed of a permeable substance. The filter 132 is preferably an acetate filter, for example. The filter 132 preferably has roughness of a degree not to pass through a material constituting the flavor source 131.

An airflow resistance of the filter 132 is preferably 5 mmAq or more and 20 mmAq or less. Accordingly, it is possible to efficiently pass through aerosol while efficiently absorbing a vapor component generated by the flavor source 131, and thus proper flavor can be supplied to a user. Further, it is possible to give a user an appropriate feeling of air resistance.

A ratio (mass ratio) between the mass of the flavor source 131 and the mass of the filter 132 is preferably in a range of 3:1 to 20:1, more preferably, in a range of 4:1 to 6:1.

The predetermined film 133 is formed integrally with the filter 132, and is composed of impermeable material. The predetermined film 133 covers a part of the outer surface of the flavor source 131 except a portion adjacent to the filter 132. The predetermined film 133 includes at least one compound selected from a group consisting of gelatin, polypropylene and polyethylene terephthalate. Gelatin, polypropylene, polyethylene and polyethylene terephthalate are not permeable, and suitable for forming a thin film. Gelatin, polypropylene, polyethylene and polyethylene terephthalate provide a sufficient resistance to moisture contained in the flavor source 131. Polypropylene, polyethylene and polyethylene terephthalate are especially excellent in a water resistance. Further, gelatin, polypropylene and polyethylene have a base resistance, and are thus hardly degraded by a basic component, even when the flavor source 131 has a basic component.

A thickness of the predetermined film 133 is preferably 0.1 μm or more and 0.3 μm or less. Accordingly, it is possible to easily break a part of the predetermined film 133 while maintaining a function of protecting the flavor source 131 by the predetermined film 133.

As described above, although the predetermined film 133 is formed integrally with the filter 132, the predetermined film 133 is bonded to the filter 132 by paste or the like. Or, by setting the outer shape of the predetermined film 133 smaller than that of the filter 132 in the vertical direction with respect to the predetermined direction A, the filter 132 may be stuffed into the predetermined film 133 and may be fitted into the predetermined film 133 by a restoring force of the filter 132. Alternatively, the filter 132 may be provided with an engagement part for engaging the predetermined film 133.

A shape of the predetermined film 133 is not particularly limited, but preferably has a concave shape in the vertical cross-section with respect to the predetermined direction A. In such a case, after filling the flavor source 131 inside the predetermined film 133 having the concave shape, an opening of the predetermined film 133 filled with the flavor source 131 is closed by the filter 132.

When the predetermined film 133 has the concave shape in the vertical cross-section with respect to the predetermined direction A, a maximum sectional area (i.e., a sectional area of an opening in which the filter 132 is fitted) of the sectional area of the space surrounded by the predetermined film 133, is preferably 25 mm$^2$ or more and 80 mm$^2$ or less, more preferably, 25 mm$^2$ or more and 55 mm$^2$ or less. In such a case, in the vertical cross-section with respect to the predetermined direction A, a sectional area of the filter 132 is preferably 25 mm$^2$ or more and 55 mm$^2$ or less. A thickness of the filter 132 in the predetermined direction A is preferably 3.0 mm or more and 7.0 mm or less.

The inhalation unit 140 has an inhalation hole 141. The inhalation hole 141 is an opening to expose the filter 132. A user inhales flavor together with aerosol by inhaling aerosol through the inhalation hole 141.

In the first embodiment, the inhalation unit 140 is configured to be attachable/detachable to/from the outer wall 124 of the atomizing unit 120. For example, the inhalation unit 140 has a cup shape configured to be fitted to an inner surface of the outer wall 124. However, the embodiment is not limited to this. The inhalation unit 140 may be attached rotatably to the outer wall 124 with a hinge or the like.

In the first embodiment, the inhalation unit 140 is provided separately from the capsule unit 130. In other words, the inhalation unit 140 constitutes a part of the main body unit. However, the embodiment is not limited to this. The inhalation unit 140 may be provided integrally with the capsule unit 130.

In such a case, it is noted that the inhalation unit 140 constitutes a part of the capsule unit 130.

(Control Circuit)

Figure 3:
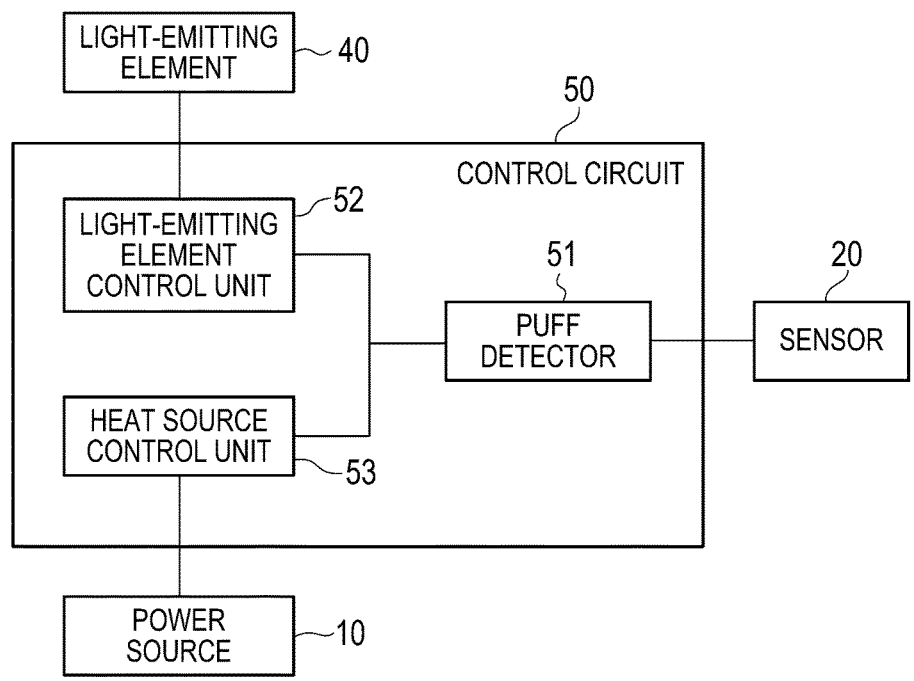
FIG. 3 is a block diagram showing a control circuit 50 according to a first embodiment.

Hereinafter, a control circuit according to a first embodiment will be explained. FIG. 3 is a block diagram showing a control circuit 50 according to a first embodiment.

As shown in FIG. 3, the control circuit 50 comprises a puff detector 51, a light-emitting element control unit 52, and a heat source control unit 53.

The puff detector 51 is connected to a sensor 20 that detects a wind pressure generated by an inhalation behavior of a user. The puff detector 51 detects a puff state based on the detection results of the sensor 20 (e.g., a negative pressure within the non-burning type flavor inhaler 100). Especially, the puff detector 51 detects a puff state inhaling an aerosol and a non-puff state not inhaling an aerosol. Thus, the puff detector 51 can specify the number of puff actions of inhaling aerosol. Further, the puff detector 51 can detect time required per one puff action of inhaling aerosol.

The light-emitting element control unit 52 is connected to the light-emitting element 40 and the puff detector 51, and controls the light-emitting element 40. Specifically, the light-emitting element control unit 52 controls the light-emitting element 40 in a first light-emitting mode, in a puff state inhaling an aerosol. On the other hand, the light-emitting element control unit 52 controls the light-emitting element 40 in a second light-emitting mode different from the first light-emitting mode, in a non-puff state not inhaling an aerosol.

Here, a light-emitting mode is defined by combination of parameters such as the amount of light of the light-emitting element 40, the number of light-emitting elements 40 in a lighting state, a color of the light-emitting element 40, and a cycle of repeating turning on and turning off of the light-emitting element 40. A different light-emitting mode means a light-emitting mode that any of the above parameters is different.

In the first embodiment, a second light-emitting mode changes according to the number of puff actions of inhaling aerosol. A first light-emitting mode may change according to the number of puff actions of inhaling aerosol, or may be constant without depending on the number of puff actions of inhaling aerosol.

For example, the first light-emitting mode is such a mode for lighting a red light-emitting element 40 to simulate a feeling of a general cigarette that generates an aerosol along with burning. The first light-emitting mode is preferably such a mode for continuously lighting the light-emitting element 40. The first light-emitting mode may be a mode of repeating turning on and turning off of the light-emitting element 40 at a first cycle. Preferably, the first light-emitting mode may be a mode for lighting a color different from a color of burning a general cigarette, i.e. a green light-emitting element 40, when emphasis on the use of the non-burning type flavor inhaler which is different from the cigarette.

For example, the second light-emitting mode is such a mode for lighting a color different from the first light-emitting mode, i.e. a blue light-emitting element 40 to notify a user that an aerosol source is not heated. The second light-emitting mode may be a mode of repeating turning on and turning off of the light-emitting element 40 at a second cycle different from the first cycle. For example, the second light-emitting mode may be a mode of repeating turning on and turning off of the light-emitting element 40 at a second cycle longer than the first cycle. In such a case, the second light-emitting mode may involve a color same as or different from the first light-emitting mode.

As described above, the second light-emitting mode changes according to the number of puff actions of inhaling aerosol.

For example, the second light-emitting mode may be a mode of increasing the number of the light-emitting elements 40 to be controlled along with an increase in the number of puff actions. For example, the light-emitting element control unit 52 controls one light-emitting element 40 in the second light-emitting mode in a first puff action, and controls two light-emitting elements 40 in the second light-emitting mode in a second puff action. Alternatively, the light-emitting element control unit 52 controls the n number of light-emitting elements 40 in the second light-emitting mode in a first puff action, and controls the n−1 number of light-emitting elements 40 in the second light-emitting mode in a second puff action.

The second light-emitting mode may be a mode for increasing or decreasing the amount of light of the light-emitting element 40 by adjusting the power amount supplied to the light-emitting element 40 along with an increase in the number of puff actions. Alternatively, the second light-emitting mode may be a light-emitting mode for changing the color of the light-emitting element 40 along with an increase in the number of puff actions.

Even in the case that the first light-emitting mode changes depending on the number of puff actions, the concept of the change of the first light-emitting mode is basically the same as the change of the second light-emitting mode.

In the first embodiment, when the number of puff actions of inhaling aerosol reaches a predetermined number (e.g., eight times), the light-emitting element control unit 52 terminates the control according to the first light-emitting mode and the second emitting mode, and controls the light-emitting element 40 in an emission end mode.

The emission end mode may be a mode to notify a user of the timing to end a puff action, and is preferably different from the first lighting-emitting mode and the second light-emitting mode. For example, the emission end mode is such a mode that the amount of light of the light-emitting element 40 is smaller than that in the first and second light-emitting modes and that the amount of light of the light-emitting element 40 is gradually decreased.

The heat source control unit 53 is connected to the power source 10, and controls the power amount supplied to the heat source 80 from the power source 10. For example, the heat source control unit 53 controls the voltage applied to the heat source 80 from the power source 10 by controlling a DC-DC converter that is added to the power source 10.

First, the heat source control unit 53 increases the power amount supplied to the heat source 80 stepwise from a reference power amount along with an increase in the number of puff actions of inhaling aerosol. Thus, it is possible to simulate a feeling of a general cigarette that generates an aerosol along with burning.

When a puff action is performed after the number of puffs exceeds a predetermined number, the heat source control unit 53 may control the power source 10 to supply the heat source 80 with the power amount smaller than the reference power amount. Thus, a user can inhale a little amount of aerosol even at the timing to end a puff action, increasing the user's satisfaction.

When a predetermined time elapses after the number of puff actions exceeds a predetermined number, the heat source control unit 53 turns off the non-burning type flavor inhaler 100. This suppresses waste of the power amount of the non-burning type flavor inhaler 100 due to forgetting to turn off the power.

The heat source control unit 53 may supply the heat source 80 with power amount smaller than the reference power amount by combining the above operations after the number of puff action exceeds a predetermined number, and may turn off the power of the non-burning type flavor inhaler 100 when a predetermined time elapses after the number of puff actions exceeds the predetermined number.

Moreover, the power of the non-burning type flavor inhaler 100 may be forced to turn off by the predetermined action of the pushbutton 30 (i.e. an action for long press of the pushbutton 30) regardless of a control of the heat source control unit 53. That is, the power of the non-burning type flavor inhaler 100 may be forced to turn off by the predetermined action of the pushbutton 30 (i.e. an action for long press of the pushbutton 30) before the puff action reaches the predetermined time.

The heat source control unit 53 preferably increases a gradient of the power amount supplied to the heat source 80 in accordance with an increase in the number of puff actions for inhaling aerosol. Here, a gradient of power amount is defined by the number of puff actions that maintains the constant power amount and by the increment step of power amount. In other words, along with an increase in the number of puff actions, the number of puff actions that maintains the constant power amount decreases. Alternatively, along with an increase in the number of puff actions, the increment step of power amount increases. Alternatively, along with an increase in the number of puff actions, the number of puff actions that maintains constant power amount decreases, and the increment step of power amount increases.

Further, the heat source control unit 53 may control a first mode using a first reference power amount as the reference power amount and a second mode using a second reference power amount greater than a first reference power amount as the reference power amount. As a reference power amount, a reference power amount of three or more steps may be prepared. In such a case, a reference power amount may be switched by operating the pushbutton 30. For example, the first mode is selected by pressing the pushbutton 30 once, and the second mode is selected by pressing the pushbutton 30 twice. The pushbutton 30 may be replaced to a touch sensor. By these operations, the power of the non-burning type flavor inhaler 100 may be turned on. In other words, turning on the power source and switching the reference power amount may be performed by one operation of the pushbutton 30. The operation of turning on the power source by operation of the pushbutton 30 may be separated from the operation of switching the reference power amount.

Second, the heat source control unit 53 controls a standard mode to be applied to a user whose required time per one puff action of inhaling aerosol is within a standard required time duration, and a reduced mode to be applied to a user whose required time per one puff action of inhaling aerosol is shorter than a standard required time duration. Here, a standard required time duration means a time duration that the balance of the inhaled amount of aerosol (TPM: Total Particulate Matter) is particularly excellent.

In particular, in one puff action in the standard mode, the heat source control unit 53 controls the power source 10 to supply the heat source 80 with a standard power amount in the duration before first duration elapses, and controls the power source 10 to supply the heat source 80 with power amount smaller than the standard power amount in the duration after first duration elapses. The power amount smaller than the standard power amount is a concept including zero, the heat source control unit 53 may immediately zeros the power amount supplied to the heat source 80, i.e. may immediately stop the power supply to the heat source 80, in the duration after the first duration elapses. Alternately, the heat source control unit 53 may gradually decrease the power amount supplied to the heat source 80.

Here, the first duration is preferably the same as an end timing of the standard required time duration. However, the first duration may be longer than the end timing of the standard required time within a range that the balance of the supplied amount of aerosol (TPM) is allowed.

On the other hand, in one puff action in the reduced mode, the heat source control unit 53 controls the power source 10 to supply the heat source 80 with first power amount greater than the standard power amount in the duration before second duration elapses, and controls the power source 10 to supply the heat source 80 with second power amount smaller than the first power amount in the duration until third duration elapses after the second duration, and controls the power source 10 to supply the heat source 80 with power amount smaller than the second power amount in the duration after the third duration elapses. The power amount smaller than the second power amount is a concept including zero, the heat source control unit 53 may immediately zeros the power amount supplied to the heat source 80, i.e. may immediately stop the power supply to the heat source 80, in the duration after the third duration elapses. Alternately, the heat source control unit 53 may gradually decrease the power amount supplied to the heat source 80.

Here, the second duration is preferably shorter than a start timing of the standard required time duration. In other words, the second duration used in the reduced mode is preferably shorter than the first duration used in the standard mode. The second duration may be included in the standard required time duration, or may be longer than the end timing of the standard required time duration. The third duration is preferably the same as the end timing of the standard required time duration. The third duration may be longer than the end timing of the standard required time duration within a range that the balance of the supplied amount of aerosol (TPM) is allowed.

The second power amount smaller than the first power amount may be the same as the standard power amount. The second power amount may either be greater than or smaller than the standard power amount.

As described above, as the number of puff actions increases, the heat source control unit 53 increases the power amount supplied to the heat source 80 stepwise from a reference power amount. In other words, it is noted that the standard power amount in one puff action increases along with an increase in the number of puff actions.

The heat source control unit 53 may set the standard mode or the reduced mode according by learning a user's puff action. In particular, when the time required per one puff action acquired by the learning is within the standard required time duration, the heat source control unit 53 sets the standard mode. When the time required per one puff action acquired by the learning is shorter than the standard required time duration, the heat source control unit 53 sets the reduced mode.

In the first embodiment, the atomizing unit 120 is attachable/detachable to/from the electrical unit 110. The capsule unit 130 is attachable/detachable to/from the main body unit including the electrical unit 110. In other words, the electrical unit 110 can be reused over multiple puff action series. A puff action series means a series of behaviors to repeat a predetermined number of puff actions. Therefore, by learning the time required per one puff action in a first puff action series, the standard mode or the reduced mode may be set in second and subsequent puff action series. Or, in one puff action series, by learning the time required per one puff action in the first n times of puff actions, the standard mode or the reduced mode may be set for the puff actions on and after n+1 (or, N+2) times.

Alternatively, the heat source control unit 53 may set the standard mode or the reduced mode according to the operation of a user. In such a case, a switch for switching the standard mode and the reduced mode is provided in the non-burning type flavor inhaler 100. It is permitted to switch the standard mode and the reduced mode in one puff action series. Alternatively, a mode that is set first may be fixedly applied without permitting switching of the standard mode and the reduced mode in one puff action series.

(Light-Emitting Mode)

Hereinafter, an example of a light-emitting mode according to the first embodiment will be explained. FIG. 4 and FIG. 5 are diagrams showing an example of a light-emitting mode according to the first embodiment. FIG. 4 and FIG. 5 show a case where a user should finish a puff action series as a rule when the number of puff actions reaches eight times (predetermined number of times).

First, a first example of a light-emitting mode will be explained with reference to FIG. 4. As shown in FIG. 4, a first light-emitting pattern in a puff state is constant without depending on the number of puff actions. On the other hand, a second light-emitting pattern in a non-puff action changes depending on the number of puff actions.

For example, as shown in FIG. 4, in the non-buff states #1 to #4, the light-emitting mode #2-1 is used as a second light-emitting mode. In the non-puff states #5 to #7, the light-emitting mode #2-2 is used as a second light-emitting mode. In the non-puff state #8, the light-emitting mode #2-3 is used as a second light-emitting mode. In the 9th non-puff state or later, the emission end mode is used.

On the other hand, in the puff states #1 to #8, the light-emitting mode #1 is used as a first light-emitting mode. In the 9th puff state or later, the light-emitting mode #1 may be used as a first light-emitting mode, or a light-emitting mode different from the first light-emitting mode and the second light emitting mode may be used to indicate that the puff exceeds eight times (predetermined number of times).

The light-emitting modes #1, #2-1, #2-2, #2-3 and the emission end mode are different each other. As described above, a light-emitting mode is defined by combination of parameters such as the amount of light of the light-emitting element 40, the number of light-emitting elements 40 in a lighting state, a color of the light-emitting element 40, and a cycle of repeating turning on and turning off of the light-emitting element 40. A different light-emitting mode means a light-emitting mode that any of the above parameters is different.

For example, the light-emitting mode #1 is preferably such a mode for imaging burning in order to simulate a feeling of a general cigarette that generates an aerosol along with burning. The light-emitting mode #2-1 is preferably such a mode for imaging the beginning of a puff action series. The light-emitting mode #2-2 is preferably such a mode for imaging the middle of a puff action series. The light-emitting mode #2-3 is preferably such a mode for imaging the end of a puff action series. The emission end mode is preferably such a mode to notify a user the timing to end a puff action.

Second, a first example of a light-emitting mode will be explained with reference to FIG. 5. As shown in FIG. 5, both the first light-emitting pattern in a puff state and the second light-emitting pattern in a non-puff state change according to the number of puff actions.

For example, as shown in FIG. 5, in a non-puff state, like the case shown in FIG. 4, the light-emitting modes #2-1, #2-2 and #2-3 are used as a second light-emitting mode.

On the other hand, in the puff states #1 to #4, the light-emitting mode #1-1 is used as a first light-emitting mode. In the puff states #5 to #7, the light-emitting mode #1-2 is used as a first light-emitting mode. In the puff state #8, the light-emitting mode #1-3 is used as a first light-emitting mode. In the 9th and subsequent puff states, the light-emitting mode #1-4 is used.

The light-emitting mode #1-1 is preferable such a light-emitting mode for imaging the beginning of a puff action series. The light-emitting mode #1-2 is preferably such a light-emitting mode for imaging the middle of a puff action series. The light-emitting mode #1-3 is preferably such a light-emitting mode for imaging the end of a puff action series. The light-emitting mode #1-4 is, like the emission end mode, preferably such a mode to notify a user the timing to end a puff action.

In the first embodiment, as shown in FIG. 4 and FIG. 5, the case where the light-emitting mode in the non-puff state #1 (i.e., the non-puff state immediately after turning on the power of the non-burning type flavor inhaler 100) is a second light-emitting mode (light-emitting mode #2-1) is described. However, the embodiment is not limited to this. A light-emitting mode in the non-puff state #1 may be an emission start mode different from the second light-emitting mode. The emission start mode is preferably such a mode to notify a user that a puff action is ready to start.

(Power Control in a Puff Action Series)

Hereinafter, an example of power control in a puff action series according to the first embodiment will be explained. FIG. 6 and FIG. 7 are diagrams showing an example of power control in a puff action series according to the first embodiment. FIG. 6 and FIG. 7 show a case where a user should finish a puff action series as a rule when the number of puff actions reaches eight times (predetermined number of times). Since power is not supplied to the heat source 80 in a non-puff state, a behavior of the power source in a non-puff state is omitted in FIG. 6 and FIG. 7.

Here, a case where the power amount supplied to the heat source 80 is controlled by the voltage applied to the heat source 80. Therefore, the power amount and the voltage can be considered as the same meaning in the first embodiment. FIG. 6 shows a first mode (low mode) using a first voltage as a reference voltage. FIG. 7 shows a second mode (high mode) using a second voltage higher than the first voltage as a reference voltage. Although the reference voltage is different, the behavior of the voltage applied to the heat source 80 is the same in the first mode (low mode) and the second mode (high mode).

As shown in FIG. 6 and FIG. 7, the heat source control unit 53 increases the voltage applied to the heat source 80 stepwise from a reference voltage along with an increase in the number of puff actions of inhaling aerosol. In particular, in the puff states #1 to #4, the voltage applied to the heat source 80 is constant, and a reference voltage is applied to the heat source 80. In the puff states #5 to #7, the voltage applied to the heat source 80 is constant, and a voltage that is one step greater than a reference voltage is applied to the heat source 80. In the puff state #8, a voltage that is two steps greater than a reference voltage is applied to the heat source 80. In the 9th or later puff state, a voltage that is smaller than a reference voltage is applied to the heat source 80.

As described above, the heat source control unit 53 increases a gradient of the voltage applied to the heat source 80 along with an increase in the number of puff actions of inhaling aerosol.

For example, as the number of puff actions increases, the number of puff actions that maintains a constant voltage decreases. In other words, the number of puff actions that a reference voltage is applied is four times, the number of puff actions that a voltage of one step greater than a reference voltage is applied is three times, and the number of puff actions that a voltage of two steps greater than a reference voltage is applied is one time. Alternatively, as the number of puff actions increases, the number of puff actions that maintains a constant voltage decreases. Alternatively, an increase width Y of second time voltage is greater than an increase width X of a first time voltage.

Thus, the gradient of voltage (θ1 and θ2), which is defined by the number of puff actions that maintains a constant voltage and by the increase width of voltage, increases along with an increase in the number of puff actions. In other words, the gradient θ2 in the middle of a puff action series is greater than the gradient θ1 at the beginning of a puff action series.

In FIG. 6 and FIG. 7, the voltage applied to the heat source 80 increases in two steps. However, the embodiment is not limited to this. The voltage applied to the heat source 80 may increase in three or more steps. Alternatively, the voltage applied to the heat source 80 may increase in one step.

(Power Control in One Puff Action)

Figure 8:
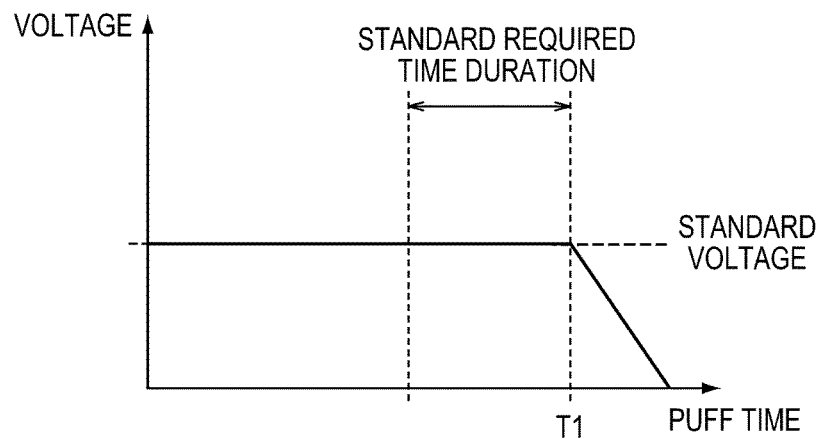
FIG. 8 is a diagram showing an example of power control in one puff action according to a first embodiment.
Figure 9:
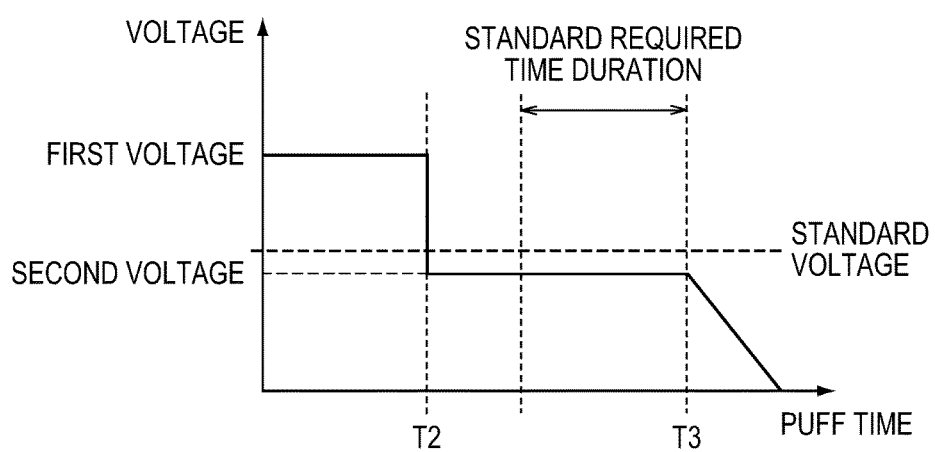
FIG. 9 is a diagram showing an example of power control in one puff action according to a first embodiment.

Hereinafter, an example of power control in a puff action series according to the first embodiment will be explained. FIG. 8 and FIG. 9 are diagrams showing an example of power control in a puff action series according to the first embodiment. FIG. 8 and FIG. 9 show a case where a user should finish a puff action series as a rule when the number of puff actions reaches eight times (predetermined number of times).

Here, a case where the power amount supplied to the heat source 80 is controlled by the voltage applied to the heat source 80. Therefore, the power and the voltage can be considered as the same meaning in the first embodiment. FIG. 8 shows a behavior of voltage applied to the heat source 80 in the standard mode. FIG. 9 shows a behavior of voltage applied to the heat source 80 in the reduced mode.

As shown in FIG. 8, in the standard mode, a standard voltage is applied to the heat source 80 in the duration before first duration T1 elapses. In the duration after the first duration T1 elapses, a voltage smaller than the standard voltage is applied to the heat source 80.

Here, the case where the first duration T1 is the same as the end timing of the standard required time duration is shown. However, as described above, the first duration T1 is not limited to this.

As shown in FIG. 9, in the reduced mode, a first voltage higher than the standard voltage is applied to the heat source 80 in the duration before second duration T2 elapses. In the duration before third duration T3 passes after the second duration T2, a second voltage smaller than the first voltage is applied to the heat source 80. In the duration after the third duration T3 elapses, a voltage smaller than the second voltage is applied to the heat source 80.

Here, the case where the second duration is shorter than the start timing of the standard required time duration is shown. The case where the third duration is the same as the end timing of the standard required time duration is shown. The case where the second voltage is smaller than the standard voltage is shown. However, the second duration T2, the third duration T3 and the second voltage are not limited to those described above.

In the case where the standard mode or the reduced mode is set, the time required per one puff action may be changed. Even in such a case, it is noted that the voltage profile shown in FIG. 8 or FIG. 9 is traced, and the voltage becomes zero immediately after the end of a puff action. In other words, because it is sufficient to control the power amount supplied to the heat source according to a predetermined operation mode, a complex control that continues controlling such supplied amount of power based on the airflow (amount of inhalation) is not necessary while the power is being supplied to the heat source 80.

(Function and Effect)

In the first embodiment, in a non-puff state not inhaling an aerosol, the light-emitting element control unit 52 controls the light-emitting element 40 in the second light-emitting mode different from the first light-emitting mode. Thus, even in a non-puff state, a user can grasp whether or not the non-burning type flavor inhaler 100 is in a usable state. Further, as a light-emitting mode in a puff state is different from a light-emitting mode in a non-puff state, it is possible to realize a feeling similar to a general cigarette that generates an aerosol along with burning.

In the first embodiment, the second light-emitting mode changes according to the number of puff actions of inhaling aerosol. Thus, a user can easily grasp a progress status of a puff according to the change of the second light-emitting mode, in a non-puff state easy to visually recognize lighting of the light-emitting element 40.

In the first embodiment, the heat source control unit 53 increases the power amount supplied to the heat source 80 stepwise from a reference power amount along with an increase in the number of puff actions of inhaling aerosol. Thus, it is possible to bring the aerosol inhalation amount close to a general cigarette that generates an aerosol along with burning, and realize a feeling similar to a general cigarette.

In the first embodiment, the heat source control unit 53 controls a first mode using a first power amount as a reference power amount, and a second mode using a second power amount greater than the first power amount as a reference power amount. Thus, a user can select the amount of aerosol depending on the taste by one non-burning type flavor inhaler 100.

In the first embodiment, as the reduced mode is used, even such a user whose required time per one puff action is shorter than the standard required time can increase the satisfaction by increasing a temperature of the heat source faster than in the standard mode. Regardless of an operation mode, as the power amount supplied to the heat source is decreased in duration after the first duration or the third duration elapses, it is possible to prevent inhalation of decomposed substance and reduction of smoking taste.

In the first embodiment, a predetermined operation mode (standard mode and reduced mode) is prepared, and it is sufficient to control the power amount supplied to the heat source according to the predetermined operation mode. Thus, a complex control that continues controlling such supplied amount of power based on the airflow (amount of inhalation) is not necessary while the power is being supplied to the heat source 80. In other words, it is possible to suppress the reduction of smoking taste, and to increase the user's satisfaction with a simple configuration.

In the first embodiment, the push button 30 is provided for switching turn on and off of the non-burning type flavor inhaler 100. Since the user can intentionally start or stop the puff action series, it is possible to realize a feeling similar to the general cigarette that generates an aerosol along with burning (a feeling of drawing line on each puff action series).

In the first embodiment, the push button 30 is provided for turning off the non-burning type flavor inhaler 100, thereby the consumption power can be reduced since the power needs not to be supplied to the sensor 20 and the light-emitting element 40 in non-used state of the non-burning type flavor inhaler 100. On the other hand, even if the push button 30 is provided for reducing the consumption power, user can grasp whether the non-burning type flavor inhaler 100 is turned on or not by the lighting mode of the light-emitting element 40. In detail, the light-emitting element 40 lights on in the non-puff stated addition to the puff state, the user can grasp the turn on of the non-burning type flavor inhaler 100 if the light-emitting element 40 emits the light, and the user can grasp the turn off of the non-burning type flavor inhaler 100 if the light-emitting element 40 does not emit the light.

[Modification 1]

Hereinafter, a modification 1 of the first embodiment will be described. Hereinafter, differences between the first embodiment and the modification 1 will be mainly described.

Specifically, in the first embodiment, the heat source control unit 53 controls the power amount supplied to the heat source 80 from the power source 10 by controlling the voltage applied to the heat source 80 from the power source 10. In detail, the heat source control unit 53 increases the power amount (voltage) supplied to the heat source 80 stepwise from the reference power amount (reference voltage) along with the increase in the number of puff actions of inhaling aerosol (see FIG. 7).

In contrast, in the modification 1, the heat source control unit 53 controls the voltage applied to the heat source 80 from the power source 10 by a pulse control, and controls the power amount supplied to the heat source 80 from the power source 10 by controlling a pulse width (duty ratio) of the voltage applied to the heat source 80. In detail, the heat source control unit 53 shortens the pulse width of the voltage applied to the heat source 80 from a reference pulse width along with the increase in the number of puff actions of inhaling aerosol (see FIG. 10).

Figure 10:
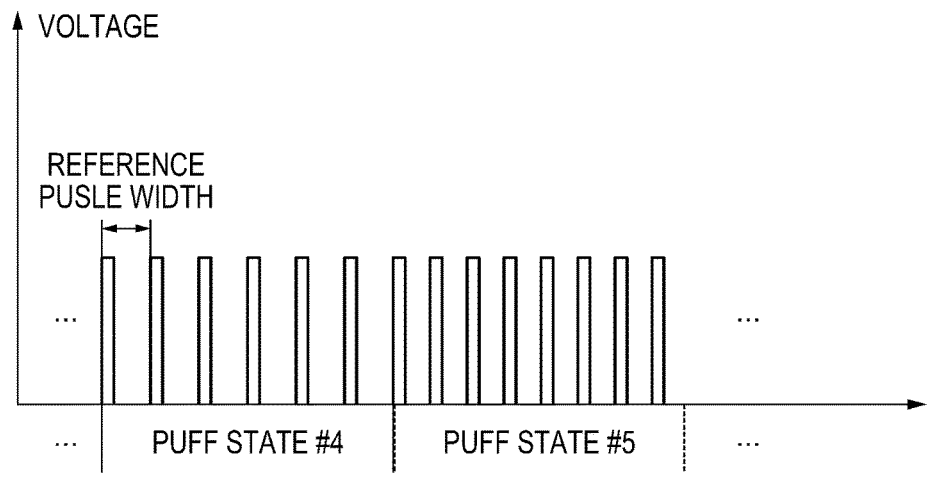
FIG. 10 is a diagram showing an example of power control in a puff action series according to a modification 1.

In the FIG. 10, a case is shown that the power amount increases between the puff state #4 and the puff state #5 following the case shown in FIG. 7. Needless to say that the effect same with the case shown in FIG. 7 can be obtained by controlling the pulse width (duty ratio), although the puff states other than the puff state #4 and the puff state #5 are omitted in FIG. 10.

[Modification 2]

Hereinafter, a modification 2 of the first embodiment will be described. Hereinafter, differences between the first embodiment and the modification 2 will be mainly described.

Specifically, in the first embodiment, the heat source control unit 53 controls the power amount supplied to the heat source 80 from the power source 10 by controlling the voltage applied to the heat source 80 from the power source 10. In detail, the heat source control unit 53 increases the power amount (voltage) supplied to the heat source 80 stepwise from the reference power amount (reference voltage) along with the increase in the number of puff actions of inhaling aerosol (see FIG. 7).

Figure 11:
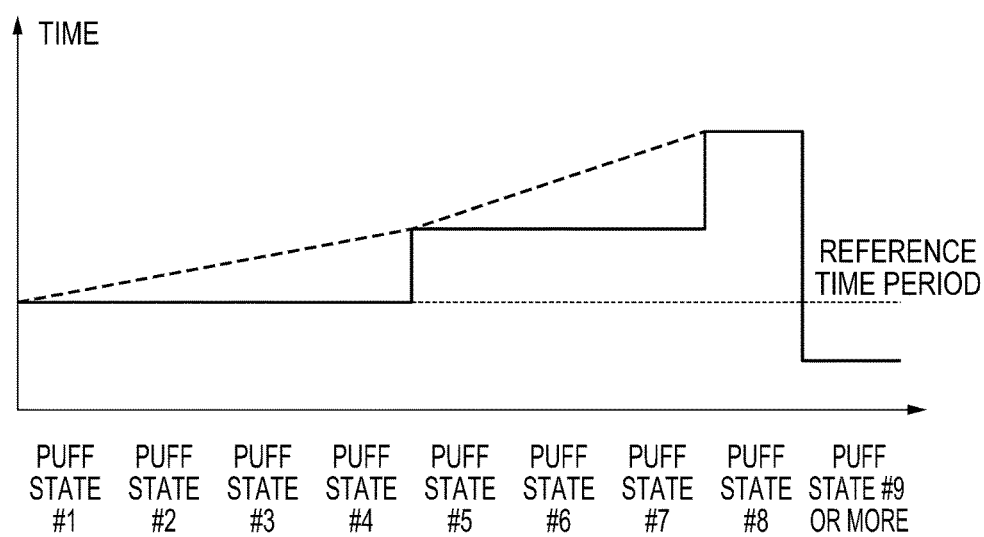
FIG. 11 is a diagram showing an example of power control in a puff action series according to a modification 2.

In contrast, in the modification 2, the heat source control unit 53 controls the power amount supplied to the heat source 80 from the power source 10 by controlling a time period of the voltage applied to the heat source 80 from the power source 10. In detail, the heat source control unit 53 lengthens the time period of the voltage applied to the heat source 80 from a reference time period along with the increase in the number of puff actions of inhaling aerosol (see FIG. 11).

In the modification 2, the reference time period means the maximum time of the continuous voltage application to the heat source 80 while the user continues the puff action. Therefore, the voltage application to the heat source 80 is stopped when a time that the user continues the puff action exceeds the reference time period. The first light-emitting mode continues while the puff action of the user continues even if the voltage application is stopped. Thereby, the effect same with the case shown in FIG. 7 can be obtained, since the total power amount supplied to the heat source 80 per one puff action changes.

When the standard mode and the reduced mode are introduced, the first duration, the second duration and the third duration may be adjusted (lengthened) along with the increase in the number of puff actions of inhaling aerosol.

[Modification 3]

Hereinafter, a modification 3 of the first embodiment will be described. Hereinafter, differences between the first embodiment and the modification 3 will be mainly described.

Specifically, the modification 3 is same with the first embodiment except for that the above-described flavor source 131 is a tobacco source.

In the modification 3, the flavor source 131 (the tobacco source) is provided at the inhalation end side than the holder 60 (aerosol source), the heat source control unit 53 increases the power amount supplied to the heat source 80 stepwise along with the increase in the number of puff actions of inhaling aerosol. Thereby, a supplied amount of nicotine component can be maintained at a level close to a supplied amount of nicotine component in the initial puff.

Specifically, a ratio of nicotine component included in aerosol is constant according to a configuration that the aerosol source includes the nicotine component such as existing electrical cigarette. Therefore, if the power amount supplied to the heat source is increased stepwise from the reference power amount for getting the supplied amount of aerosol closer to the general cigarette using such configuration, a supplied amount of nicotine component increases in proportion to the supplied amount of aerosol.

In contrast, the modification 3 introduces a configuration that the tobacco source is provided at the inhalation end side than the holder 60 (aerosol source). The inventers find out that the supplied amount of nicotine component decreases along with the increase in the number of puff actions. Thereby, the supplied amount of nicotine component can be maintained at the level close to the supplied amount of nicotine component in the initial puff As described above, in the configuration that the tobacco source is provided at the inhalation end side than the holder 60 (aerosol source) according to the modification 3, the heat source control unit 53 increases the power amount supplied to the heat source 80 stepwise along with the increase in the number of puff actions of inhaling aerosol. Thereby, the supplied amount of nicotine component can be maintained at the level close to the supplied amount of nicotine component in the initial puff while the supplied amount of aerosol becomes closer to the general cigarette.

[Modification 4]

Hereinafter, a modification 4 of the first embodiment will be described. Hereinafter, differences from the modification 3 will be mainly described.

Specifically, the modification 4 is same with the modification 3 except that the tobacco source includes at least one kind of stabilization agent stabilizes a delivery of nicotine component included in the tobacco source.

In detail, the tobacco source includes at least one kind of stabilization agent stabilizes the delivery of nicotine component included in the tobacco source in the modification 4. The stabilization agent has characteristics that a solubility parameter distance to the nicotine component is 17 or less and a vapor pressure at 25° C. is 1 mmHg or less.

The stabilization agent preferably has characteristics that a solubility parameter distance to the nicotine component is 17 or less and a vapor pressure at 25° C. is 0.1 mmHg or less.

In detail, the solubility parameter distance is an index showing a solubility of solute to solvent, generally expressed as Ra (MPa$_{1/2}$). Ra can be calculated based on following equation.

$$Ra = [4*(\delta d,2-\delta d,1)^2 + (\delta p,2-\delta p,1)^2 + (\delta h,2-\delta h,1)^2]^{(1/2)}$$

Here, δd, δp and δh are defined as follow.

δd=Dispersion force of solubility parameter
δp=Dipole interaction of solubility parameter δh=Hydrogen bond of solubility parameter As the stabilization agent satisfied above condition, one or more material selected from propylene glycol, benzyl alcohol and a compound of ester function. For example, one or more material selected from medium-chain triglyceride, triester citrate (triethyl citrate, tributyl citrate, and so on), benzyl benzoate and ethyl laurate can be used.

As shown in Table 1 below, the solubility parameter distance Ra and the vapor pressure at 25° C. of above described stabilization agent with glycerin (A).

TABLE 1

| Stabilization agent | Ra ($MPa^{1/2}$ at 25° C.) | Vapor pressure (mmHg at 25° C.) |
|---|---|---|
| A (Glycerin) | 23.0 | 0.0002 |
| B (Propylene glycol) | 16.4 | 0.2 |
| C (Medium-chain triglyceride) | 11.7 | 0.0000000002 |
| D (Triethyl citrate) | 5.7 | 0.0002 |
| E (Benzyl benzoate) | 1.3 | 0.0003 |
| F (Benzyl alcohol) | 6.6 | 0.2 |
| G (Ethyl laurate) | 9.0 | 0.00744 |
| H (Tributyl citrate) | 8.6 | 0.0000001 |

Here, the solubility parameter distance Ra shown in Table 1 is a value calculated by use of Molecular Modeling Pro Version 6.01. A decrease in the delivery of nicotine component along with the increase in the number of puff actions is suppressed by using samples (B) to (H) except for glycerin (A) (see WO2012/133289).

Here, as disclosed in WO2012/133289, a degree of suppressing the decrease in the delivery of nicotine component along with the increase in the number of puff actions is different by kind or amount of the stabilization agent included in the tobacco source.

In the modification 4, the tobacco source includes the stabilization agent has characteristics that a solubility parameter distance to the nicotine component is 17 or less and a vapor pressure at 25° C. is 1 mmHg or less. Thereby, the decrement amount of the delivery of nicotine component slows down along with the increase in the number of puff actions, the increment amount of the power amount supplied to the heat source 80 can be reduced. That is, when the power source 10 is provided in the limited space and the power amount supplied from the power source 10 is restricted, it is easy to adjust the power amount supplied from the power source.

[Experiment Result 1]

Hereinafter, an experiment 1 will be described. In the experiment 1, samples of example and comparative example were prepared as the non-burning type flavor inhaler. Amounts of nicotine and glycerin regarding the samples of example and comparative example were measured by use of a measurement apparatus shown in FIG. 12. Specifically, the amounts of nicotine and glycerin were measured by applying a voltage to the samples of example and comparative example at a constant level (2.8 V) (Constant voltage). The amounts of nicotine and glycerin were measured by applying a voltage to the samples of example and comparative example in an increased manner shown in Table 2 (Gradient).

TABLE 2

| Number of puffs actions | 1-5 | 6-10 | 11-15 | 16-20 |
|---|---|---|---|---|
| Voltage (V) | 2.80 | 2.95 | 3.10 | 3.25 |

(Each Samples)

First, as the sample of example, prepared was the non-burning type flavor inhaler having the electrical unit 110 and the atomizing unit 120 as shown in FIGS. 1 and 2 according to the first embodiment. In the sample of example, a PET resin web (Unitika Trading Co., Ltd) was used as the holder 60. A solution including glycerin and pure water at a ratio of 9:1 was used as the aerosol source, a glass yarn (Siliglass, Nippon Muki Co., Ltd) was used as the absorber 70, and a resistance heating wire made of nichrome type two (resistance=2.3Ω) was used as the heat source 80.

In the capsule unit 130, an acetate filter extended in a longitudinal direction by 5 mm was used as the filter 132, a gelatin capsule (food use capsule 00, Qualicaps Co., Ltd.) was used as the predetermined film 133. Potassium carbonate was added to the tobacco material, and pH of the tobacco material added the potassium carbonate was adjusted to 9.4. Such tobacco material was crashed into grain having a grain diameter of 0.2 mm to 0.7 mm, crashed tobacco material was filled in the capsule unit 130. A leaf tobacco contains nicotine of 2.2 wt % was used as the tobacco material, and a filling amount of tobacco material was adjusted so that amount of nicotine component included in the tobacco source becomes 3.5 mg in that the tobacco material is filled in the capsule unit 130.

Second, as the sample of comparative example, prepared was a non-burning type flavor inhaler where a nicotine component is included in an aerosol source and a tobacco source is not provided at an inhalation end side than the aerosol source. The sample of comparative example is same with the sample of example except for the following issue. A solution was used as the aerosol source that the nicotine component is added to the above-described mixed solution of glycerin and water so that a concentration of nicotine component becomes 4 wt %, and the capsule unit 130 is not provided.

(Measurement Method)

Figure 12:
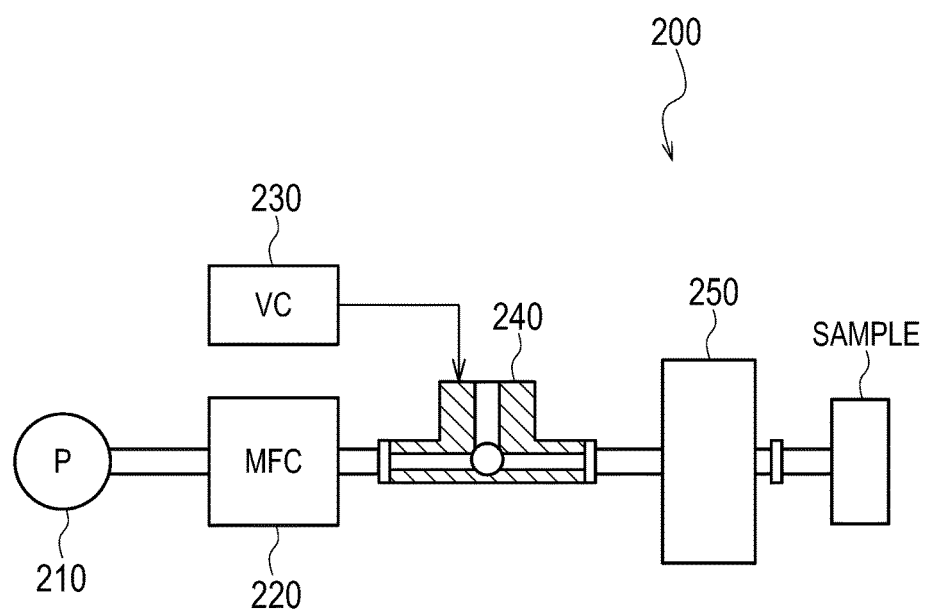
FIG. 12 is a diagram showing a measurement apparatus used in an experiment.

As shown in FIG. 12, the measurement apparatus 200 includes a suction pump 210, a mass flow controller (MFC) 220, a valve controller 230, a solenoid valve 240 and a cambridge filter 250. Each of the samples is connected to the cambridge filter 250, and amount of nicotine component and amount of glycerin (supplied amount of aerosol) were measured for an accumulated number of puff actions.

Specifically, the suction pump 210 and the cambridge filter 250 were connected for 2 seconds by opening and closing operation of the solenoid valve 240 controlled the valve controller 230, and thereafter, the cambridge filter 250 was released into the air for 13 seconds. Assuming such operation as one pseudo puff action, the pseudo puff actions were repeated for 20 times. A flow amount of the mass flow controller 220 is set to 1650 cc/minute.

Using such measurement apparatus 200, the cambridge filter 250 was changed for each five puff actions. The cambridge filter 250 was subjected to a shaking extraction by EtOH solution of 10 mL, the amount of nicotine component and the amount of glycerin (supplied amount of aerosol) were determined by use of GC/MC. Subsequently, the amount of nicotine component and the amount of glycerin per one puff action was calculated by dividing determined amount of nicotine component and glycerin by 5 times.

(Experiment Result)

Figure 13:
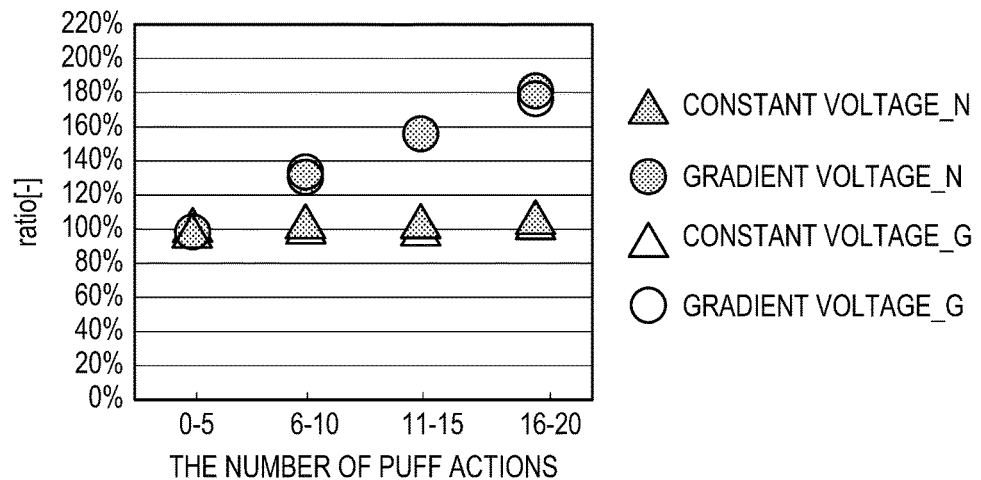
FIG. 13 is a diagram showing an experiment result 1.
Figure 14:
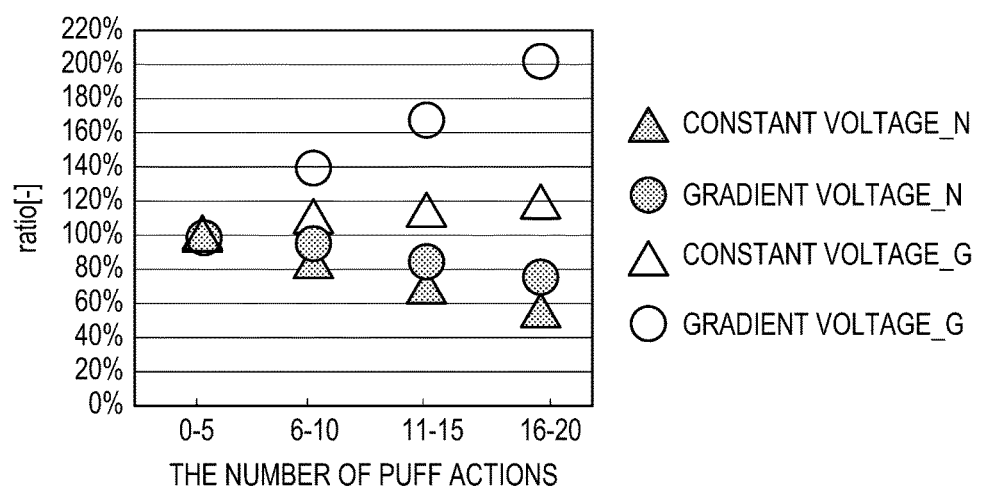
FIG. 14 is a diagram showing an experiment result 1.

An experiment result of the sample of the comparative example is shown in FIG. 13, and an experiment result of the sample of the example is shown in FIG. 14. In the FIGS. 13 and 14, assuming the measurement result for the initial 5 times as 100%, the measurement results for 5-10 times, 11-15 times and 15-20 times are shown in a ratio.

As shown in FIG. 13, according to the sample of the comparative example, the amount of nicotine component (Constant voltage_N) and the amount of glycerin (Constant voltage_G) were constant regardless of the number of puff actions when the voltage applied to the sample is constant. On the other hand, as shown in FIG. 13, the amount of nicotine component (Gradient_N) and the amount of glycerin (Gradient_G) were increased as the number of puff actions increase when the voltage applied to the sample is increased.

As shown in FIG. 14, according to the sample of the example, although the amount of glycerin (Constant voltage_G) was constant regardless of the number of puff actions but the amount of nicotine component (Constant voltage_N) was decreased as the number of puff actions increase, when the voltage applied to the sample is constant.

In contrast, as shown in FIG. 14, the amount of glycerin (Gradient_G) was increased as the number of puff actions increase and the amount of nicotine component (Gradient_N) was decreased as the number of puff actions increase. Note that it was confirmed that the decrement amount of the amount of nicotine component (Gradient_N) is less than the decrement amount of the amount of nicotine component (Constant voltage_N).

As described above, according to the sample of the example, it was confirmed that the decrement of the amount of nicotine component can be suppressed regardless of the number of puff actions while the amount of glycerin increases by the increment of the number of puff actions, by increasing the voltage applied to the sample. That is, the supplied amount of the nicotine component can be kept at the level close to initial puff while realizing the aerosol supply behavior similar to the general cigarette.

[Experiment Result 2]

Hereinafter, an experiment result 2 will be described. In the experiment 2, prepared were samples having different additive amount of the stabilization agent included in the tobacco source. A configuration of the sample prepared in the experiment 2 is same with a configuration of the sample prepared in the experiment 1. The triethyl citrate was added as the stabilization agent. The additive amounts of the triethyl citrate are 0 wt %, 5 wt %, 10 wt % and 20 wt % respectively assuming the tobacco source as 100 wt %.

The amount of nicotine component and the amount of glycerin were measured by increasing the voltage applied to respective samples of four type according to the above-described Table 2. The measurement method of the amount of nicotine component and the amount of glycerin was same with the experiment 1. Measurement results of the amount of nicotine component were shown in FIG. 15 and measurement results of the amount of glycerin were shown in FIG. 16.

Figure 15:
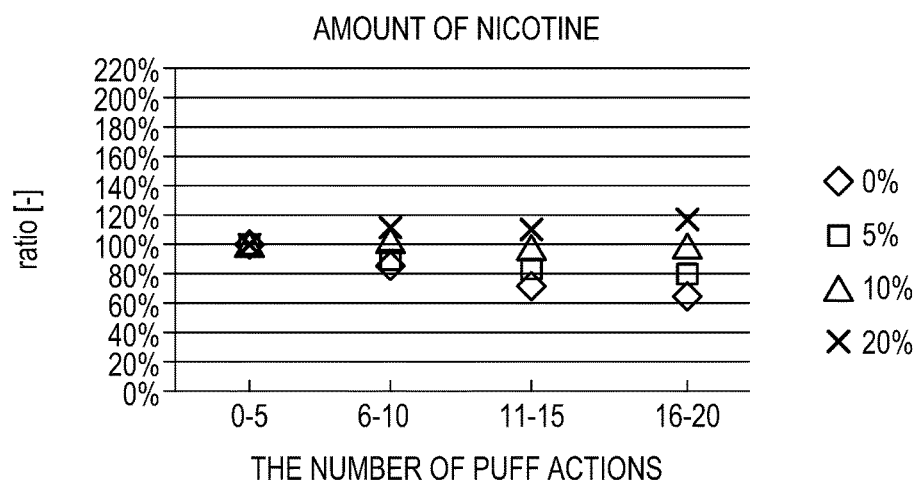
FIG. 15 is a diagram showing an experiment result 2.
Figure 16:
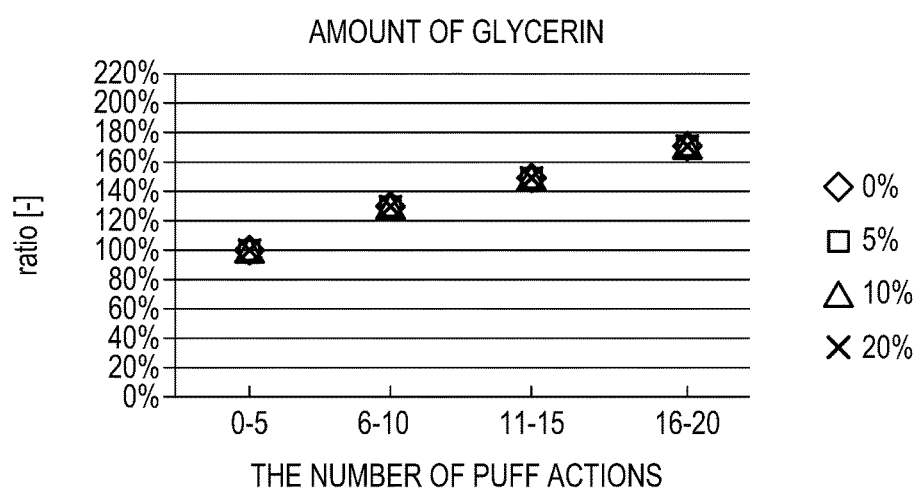
FIG. 16 is a diagram showing an experiment result 2.

As shown in FIG. 15, it is confirmed that the decrement amount of the delivery amount of nicotine component slows down according to the increment of the number of puff actions as the additive amount of the triethyl citrate becomes larger. On the other hand, as shown in FIG. 16, the amount of glycerin (the supplied amount of aerosol) increases according to the increment of the number of puff actions regardless of the additive amount of the triethyl citrate.

As described above, according to the sample of the example, it was confirmed that the decrement amount of the delivery amount of nicotine component slows down according to the increment of the number of puff actions by increasing the additive amount of the triethyl citrate, and the power amount supplied to the power source can be reduced. That is, when the power source 10 is provided in the limited space and the power amount supplied from the power source 10 is restricted, it was confirmed to easily adjust the power amount supplied from the power source.

Moreover, it was same with the experiment 1 that the amount of glycerin (the supplied amount of aerosol) increases according to the increment of the number of puff actions regardless of the additive amount of the triethyl citrate. Therefore, it was confirmed that the aerosol supply behavior similar to the general cigarette can be copied by a combination of the addition of triethyl citrate and the increment of the voltage applied to the sample.

[Other Embodiments]

The present invention has been explained according to the embodiment described hereinbefore. However, the description and drawings constituting a part of the disclosure are not to be understood to limit the invention. Various alternative embodiments, examples, and operational techniques will be apparent to those skilled in the art from this disclosure.

In the embodiment, the capsule unit 130 is used as a member for containing the flavor source 131. However, the embodiment is not limited to this. The member for containing the flavor source 131 may be a member at least having a structure that can deliver the aerosol to the user via the flavor source 131 (a structure that the aerosol generating source and the outlet is communicated via the flavor source), when it becomes a usable state that the member is connected to the main body unit. For example, it may be a cartridge. In such a case, the cartridge includes a cylindrical member, a pair of filters each provided at respective end of the cylindrical member, and a flavor source 131 filled in a space partitioned by the cylindrical member and the pair of filters.

Although not specifically mentioned in the embodiment, the number of puff actions may be corrected by the value (amount of generated aerosol) defined by the time required per one puff action and by the amount of power supplied to the heat source 80. In particular, when the amount of aerosol generated per one puff action is smaller than a predetermined value, the number of puff actions may be accumulated by adding a predetermined coefficient $\alpha$ ($\alpha<1$) to the value multiplied in one time. On the other hand, when the amount of aerosol generated per one puff action is greater than a predetermined value, the number of puff actions may be accumulated by adding a predetermined coefficient $\beta$ ($\beta>1$) to the value multiplied in one time. Namely, the number of puff actions may not necessarily be an integer.

Although not specifically mentioned in the embodiment, the timing to increase the amount of power supplied to the heat source 80 in power control in a puff action series is preferably synchronized with the timing to change the second light-emitting mode. For example, as shown in FIGS. 6 and 7, when the amount of power (voltage) supplied to the heat source 80 increases between the puff states #4 and #5, the second light-emitting mode preferably changes between the puff states #4 and #5.

Although not specifically mentioned in the embodiment, as shown in FIGS. 8 and 9, a voltage smaller than a standard voltage is applied to the heat source 80 in the duration after the first duration T1 or the third duration T3 elapses. Even in such a duration, the first light-emitting mode preferably continues.

In the embodiment, there is provided a first mode using a first reference amount of power as a reference amount of power (Low mode in FIG. 6), and a second mode using a second reference amount of power greater than the first reference amount of power (High mode in FIG. 7). In such a case, a light-emitting mode in the first mode may be different from a light-emitting mode in the second mode. In other words, the first light-emitting mode, the second light-emitting mode and the emission end mode in the first mode may be different from the first light-emitting mode, the second light-emitting mode and the emission end mode in the second mode.

Although not specifically mentioned in the embodiment, the switching of the puff action series preferably performed as follow.

(a) A case where the non-burning type flavor inhaler 100 automatically turned off by the control of the control circuit 50 when the number of puff actions in the puff action series reaches the predetermined number of times In such a case, the new puff action series starts when the non-burning type flavor inhaler 100 turned on again.

(b) A case where the non-burning type flavor inhaler 100 automatically turned off by the control of the control circuit 50 when the inhalation is not performed for a predetermined period (for example, shortest period among "a predetermined number*60 seconds", "15 minutes" and "a time from when the number of puff actions exceeds the predetermined number of times to when it turned off automatically (i.e. the above predetermined times)*2") before the number of puff actions in the puff action series reaches the predetermined number of times In such a case, the new puff action series starts when the number of puff actions is equal to or more than a switch determination times (i.e. ½ or the predetermined times). On the other hand, the previous puff action series continues when the number of puff actions is less than a switch determination times (i.e. ½ or the predetermined times).

(c) A case where the non-burning type flavor inhaler 100 forced to turn off by the predetermined action of the pushbutton 30 (i.e. an action for long press of the pushbutton 30)

In such a case, the new puff action series starts when the non-burning type flavor inhaler 100 turned on again. Alternately, it may be selectable for user to start the new puff action series or continue the previous puff action series when the non-burning type flavor inhaler 100 turned on again.

In the cases (a) and (c) described above, the number of the puff actions counted during the puff action series may be reset at the timing of turning off the non-burning type flavor inhaler 100. Alternately, the number of the puff actions counted during the puff action series may be reset at the timing of turning on the non-burning type flavor inhaler 100 again. In the case (c) described above, if a configuration is introduced that the user can select to start the new puff action series or continue the previous puff action series, the number of the puff actions counted during the puff action series may be reset when the non-burning type flavor inhaler 100 is turned on again and the user selects to start the new puff action series.

On the other hand, in the case (b) described above, the number of the puff actions counted during the puff action series may be reset when the number of puff actions is equal to or more than the switch determination times and the non-burning type flavor inhaler 100 is turned off. Alternately, the number of the puff actions counted during the puff action series may be reset when the number of puff actions is equal to or more than the switch determination times and the non-burning type flavor inhaler 100 is turned on again.

In the embodiment, a case is exampled that the pushbutton 30 is provided as a user interface for turning on or turning off the power of the non-burning type flavor inhaler 100. However, the embodiment is not limited to this. The user interface for turning on or turning off the power of the non-burning type flavor inhaler 100 may be a hardware switch enables to turning on or turning off the non-burning type flavor inhaler 100 without power consumption.

In the embodiment, the non-burning type flavor inhaler 100 is exampled that including the pushbutton 30 for turning on. However, the embodiment is not limited to this. The non-burning type flavor inhaler 100 may not include the pushbutton 30 for turning on. In such a case, the end of the puff action series may be notified to the user by only the emission end mode of the light-emitting element 40 instead of turning off the non-burning type flavor inhaler 100 like the above described embodiment, when the number of puff actions exceeds the predetermined number of times and the predetermined time elapses. Similarly, the control may be performed that the power supply to the heater source 80 is restricted even if the sensor 20 detects the user inhalation for a predetermined period (i.e. 5 minutes) instead of turning off the non-burning type flavor inhaler 100.

Although the heat source 80 is exampled as the atomizer atomizing the aerosol source without burning in the embodiment, the embodiment is not limited to this. The atomizer atomizing the aerosol source without burning may be a unit atomizing the aerosol source by ultrasonic.

It is noted that the entire content of Japan Patent Application No. 2013-204190 (filed on Sep. 30, 2013), Japan Patent Application No. 2014-14190 (filed on Jan. 29, 2014), Japan Patent Application No. 2014-14201 (filed on Jan. 29, 2014) and Japan Patent Application No. 2014-14208 (filed on Jan. 29, 2014) are incorporated in the present application by reference.

INDUSTRIAL APPLICABILITY

According to the present invention, it is possible to provide a non-burning type flavor inhaler that can realizes a feeling of use like a feeling of use of a general cigarette.

The invention claimed is:

1. A non-burning type flavor inhaler having a shape extending from a non-inhalation end toward an inhalation end along a predetermined direction, comprising:
    an aerosol source that generates an aerosol;
    an atomizer that atomizes the aerosol source without burning;
    a power source that supplies power to the atomizer; and
    a control unit that controls a power amount supplied from the power source to the atomizer, wherein
    the control unit increases the power amount supplied to the atomizer stepwise from a reference power amount along with an increase in the number of puff actions for inhaling the aerosol.

2. The non-burning type flavor inhaler according to claim 1, wherein
    the control unit controls a first mode using a first reference power amount as the reference power amount, and a second mode using a second reference power amount greater than the first reference power amount.

3. The non-burning type flavor inhaler according to claim 1, wherein
    the control unit controls the power source to supply the atomizer with the power amount smaller than the reference power amount, when the puff action is performed after the number of puff actions exceeds a predetermined number.

4. The non-burning type flavor inhaler according to claim 3, wherein
the control unit turns off the power of the non-burning type flavor inhaler, when a predetermined time elapse after the number of puff actions exceeds the predetermined number.

5. The non-burning type flavor inhaler according to claim 1, wherein
the control unit increases a gradient of the power amount supplied to the atomizer along with the increase in the number of puff actions of inhaling the aerosol.

6. The non-burning type flavor inhaler according to claim 1, comprising:
a light-emitting element, wherein
the control unit controls the light-emitting element in a first light-emitting mode in a puff state inhaling the aerosol, and controls the light-emitting element in a second light-emitting mode different from the first light-emitting mode in a non-puff state not inhaling the aerosol, and
the second light-emitting mode changes according to the number of puff actions for inhaling the aerosol, and
a timing of increasing the power amount supplied to the atomizer is synchronized with a timing of changing the second light-emitting mode.

7. The non-burning type flavor inhaler according to claim 1, wherein
the number of puff actions is corrected by a value defined by the time required per one puff action and the power amount supplied to the heat source.

8. The non-burning type flavor inhaler according to claim 2, wherein
a switching between the first mode and the second mode is performed by an operation of a pushbutton or a touch sensor.

9. The non-burning type flavor inhaler according to claim 8, wherein
the power of the non-burning type flavor inhaler is turned on by the operation of the switching between the first mode and the second mode.

10. The non-burning type flavor inhaler according to claim 1, comprising:
a tobacco source provided at the non-inhalation end side than the aerosol source.

11. The non-burning type flavor inhaler according to claim 10, wherein
the tobacco source includes a stabilization agent stabilizes the delivery of nicotine component included in the tobacco source, and
the stabilization agent has characteristics that a solubility parameter distance to the nicotine component is 17 or less and a vapor pressure at 25° C. is 1 mmHg or less.

12. The non-burning type flavor inhaler according to claim 1, comprising:
a hardware switch for performing at least one of turning on and turning off the non-burning type flavor inhaler.

13. The non-burning type flavor inhaler according to claim 1, wherein
the number of puff actions reset in response to turning on and turning off the non-burning type flavor inhaler.

14. The non-burning type flavor inhaler according to claim 1, wherein
the atomizer is a heat source that heats the aerosol source without burning.

* * * * *